United States Patent
Jakob et al.

(10) Patent No.: US 7,566,169 B2
(45) Date of Patent: Jul. 28, 2009

(54) TRANSPORTABLE FLAT X-RAY DETECTOR

(75) Inventors: Rudolf Jakob, Uttenreuth (DE);
Thomas Schmitt, Forchheim (DE);
Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/405,443

(22) Filed: Apr. 18, 2006

(65) Prior Publication Data

US 2006/0239412 A1  Oct. 26, 2006

(30) Foreign Application Priority Data

Apr. 18, 2005  (DE) .................. 10 2005 017 944

(51) Int. Cl.
*H01J 31/50* (2006.01)
*H05G 1/64* (2006.01)

(52) U.S. Cl. ..................... 378/189; 378/98.8
(58) Field of Classification Search ................ 378/19, 378/22, 98.8, 167–169, 182, 189
See application file for complete search history.

(56) References Cited

U.S. PATENT DOCUMENTS 5,539,799 A    7/1996   Siemens

| | | | |
|---|---|---|---|
| 6,533,453 B1* | 3/2003 | Heidsieck et al. | 378/189 |
| 6,805,484 B2* | 10/2004 | Kuramoto et al. | 378/189 |
| 7,104,686 B2* | 9/2006 | Watanabe et al. | 378/189 |
| 7,189,972 B2* | 3/2007 | Ertel et al. | 250/370.11 |
| 2001/0022719 A1* | 9/2001 | Armitage et al. | 361/681 |

FOREIGN PATENT DOCUMENTS

DE   42 38 268 C2   7/1998
EP   1 643 305 A1   4/2006

OTHER PUBLICATIONS

Sirona—The Dental Company: "SIDEXIS-Intraoral sensors", Sirona—The Dental Company—Products—imaging systems - Intraoral X-Ray—Intraoral sensors: im Internet: www.sirona.com/ecomaXL/index.php, Feb. 22, 2006.
Spahn, Martin —Heer, Volker—Freytag, R.: Flachbilddetektoren in der Rëntgendiagnostik, Der Radiologe May 2003 Radiologa 2003 • vol. 43, Seiten 340-350.

* cited by examiner

*Primary Examiner*—Irakli Kiknadze
(74) *Attorney, Agent, or Firm*—Harness, Dickey & Pierce PLC

(57) ABSTRACT

A transportable flat X-ray detector includes a housing with a grip and an active surface with a scintillator layer and semiconductor layer including a multiplicity of pixel elements arranged in a matrix. Further, gripping elements such as gripping holes, depressions, pits or gripping troughs are provided in the housing at the edge of the flat X-ray detector, outside the active surface.

19 Claims, 5 Drawing Sheets

TRANSPORTABLE FLAT X-RAY DETECTOR

The present application hereby claims priority under 35 U.S.C. §119 on German patent application number DE 10 2005 017 944.4 filed Apr. 18, 2005, the entire contents of which is hereby incorporated herein by reference.

FIELD

The invention generally relates to a transportable flat X-ray detector. For example, it may relate to one including a housing with a grip and an active surface with a scintillator layer and semiconductor layer that includes a multiplicity of pixel elements arranged in a matrix.

BACKGROUND

Digital flat X-ray detectors have been changing classic radiography or fluoroscopy, angiography and cardanigiography for years. The most varied technologies, including digital ones, have already been in use in part for a long time, examples being image intensifier camera systems based on television or CCD cameras, storage film systems with an integrated or external readout unit, systems with optical coupling of the converter foil to CCDs or CMOS chips, selenium-based detectors with electrostatic readout (for example Thoravision) and solid-state detectors with active readout matrices and direct or indirect conversion of the X-radiation.

In particular, novel solid-state detectors (FD) for digital X-ray imaging have been undergoing introduction to the markets for a few years; these are based on active readout matrices, for example made from amorphous silicon (a-Si). The image information is converted in an X-ray converter, for example caesium iodide (CsI), stored in the photodiodes of the matrix as electric charge, and subsequently read out via an active switch element with the aid of dedicated electronics, subjected to analog-to-digital conversion and processed further by the image system.

Related technologies likewise employ an active readout matrix made from amorphous silicon, but a converter (for example selenium) that directly generates electrical charge that is then stored on an electrode. The stored charge is subsequently read out in order to generate an image signal. Other technologies are based on CCDs (charge coupled devices) or APS (active pixel sensor) or large-area CMOS chips, as described, for example, in Spahn et al., "Röntgen-Flachdetektoren in der Röntgendiagnostik" ["Flat X-ray detectors in X-ray diagnostics"], Radiologe 43 (2003), pages 340 to 350.

Portable flat X-ray detectors have also recently become available. These are used both for free images and for so-called bed lungs. In the technical jargon, bed lungs are pulmonary images taken with the aid of a mobile X-ray diagnostic device in the bed.

Particularly in the case of these bed lungs, but also, however, in the case of other applications, the detector is placed completely below the patient. This may include, for example, a handle that is attached on the longitudinal side of the flat X-ray detector and lies transverse to the bed. Above all else, it is difficult with patients who are older, traumatized or otherwise difficult to move for handling to be carried out below the patient, to place the flat X-ray detector and to remove it. Such a flat X-ray detector having a grip is known, for example, from the brochure by Siemens Medical Solutions entitled "AXIOM Multix M Your portal to the world of direct digital radiography" with order number A91100-M1200-B527-2-7600.

SUMMARY

An object of at least one embodiment of the application includes designing a transportable flat X-ray detector in such a way that the flat X-ray detector can be more easily operated, for example in the case of bed-based imaging.

An object may be achieved according to at least one embodiment of the invention by virtue of the fact that gripping elements are provided in the housing at the edge of the flat X-ray detector outside the active surface. This yields a transportable flat X-ray detector having additional gripping elements for simple handling, in particular in the case of bed lungs.

It has proved to be advantageous when the gripping elements are holes and/or alternatively depressions, pits or troughs.

According to at least one embodiment of the invention, the gripping elements can be arranged in the corners of the flat X-ray detector.

The additional gripping elements interfere the least in the detector design when they are arranged on both sides next to the grip.

The gripping elements can advantageously have a diameter of the size of a finger.

BRIEF DESCRIPTION OF THE DRAWINGS

The invention is explained below in more detail with the aid of example embodiments illustrated in the drawings, in which.

DETAILED DESCRIPTION OF THE EXAMPLE EMBODIMENTS

Figure 1:
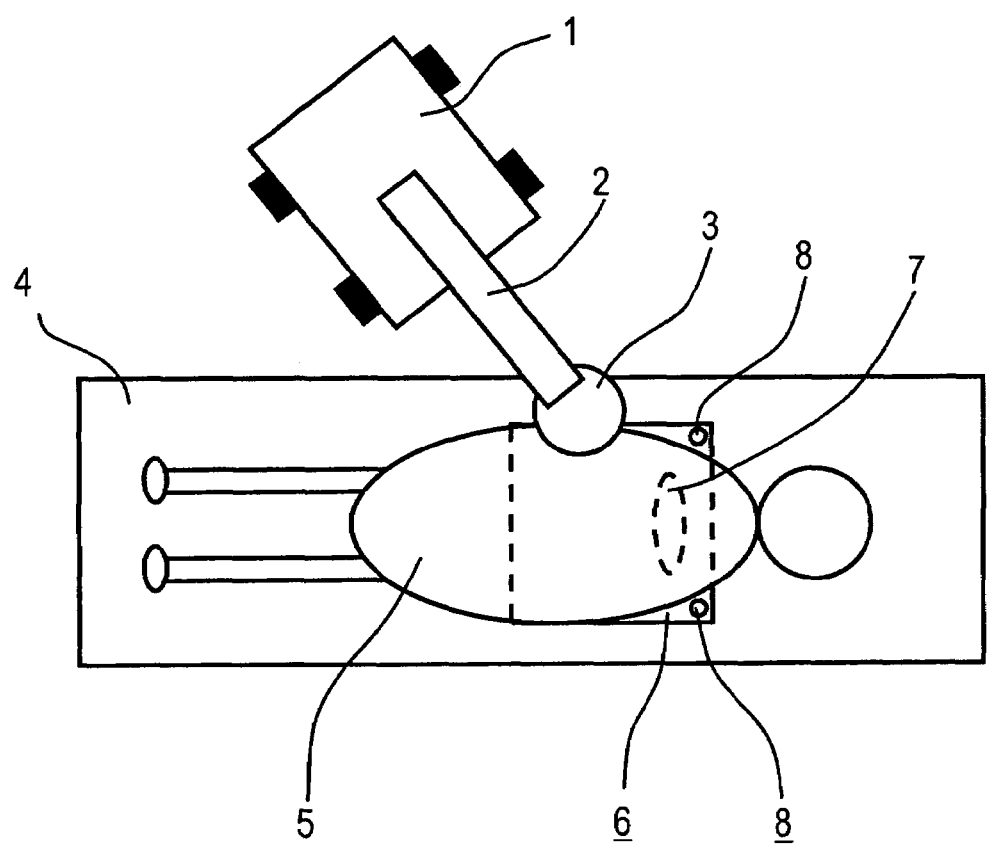
FIG. 1 shows a schematic of a mobile X-ray diagnostic device having a mobile flat X-ray detector according to at least one embodiment of the invention.

FIG. 1 is a schematic of a mobile X-ray diagnostic device having an X-ray generator 1 on which an X-ray emitter 3 is attached via a support arm 2. A patient 5 lying in a bed or on a patient support table 4 is intended to be transirradiated. Arranged below the patient 5 is a mobile flat X-ray detector 6. On its long side, the latter has a grip 7 by which it can be carried and can be placed for taking an image, for example a bed lung. Next to the patient 5 and the grip 7, the flat X-ray detector 6 has on the side gripping elements, for example gripping holes 8, whose mode of operation is further described below. Instead of the gripping holes 8, it is also possible to provide depressions, pits and/or gripping troughs.

Figure 2:
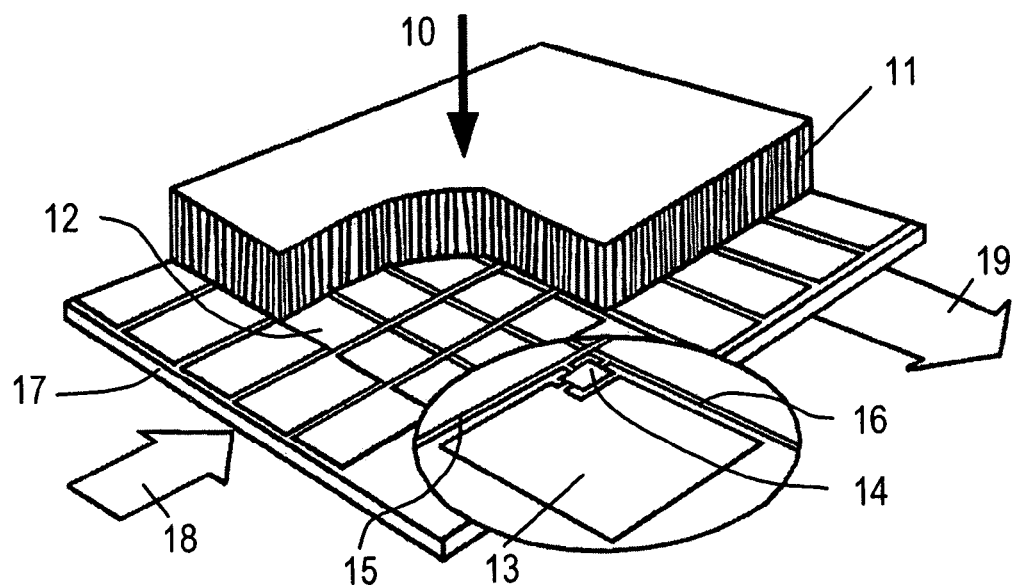
FIG. 2 shows a schematic of a solid state detector.

The flat X-ray detector 6 is illustrated in perspective cross section in FIG. 2. The core component of the flat X-ray detector 6 includes a solid state pixel matrix, line drivers and amplifiers. The solid state pixel matrix has, for example, a layer with a scintillator 11, for example consisting of caesium iodide (CsI), that when struck with X-radiation 10 feeds into a pixel matrix 12 made from amorphous silicon photons that produce a visible X-ray image. As illustrated in an enlarged fashion in FIG. 2, each of the pixels of this pixel matrix 12 includes a photodiode 13 and a switch 14 that is connected to row lines 15 and column lines 16. The pixel matrix 12 is applied to a glass substrate 17.

All the pixels of a row are respectively simultaneously addressed and read out by the driving circuits 18. In the simplest case, an image is read out progressively row by row. The signals are fed to a processing circuit via readout electronics 19 in which the signals are processed in parallel in a multiplicity of amplifiers, brought together by multiplexers and converted in an analog-to-digital converter (A/D converter) to form a digital output signal for the purpose of further digital processing.

Figure 3:
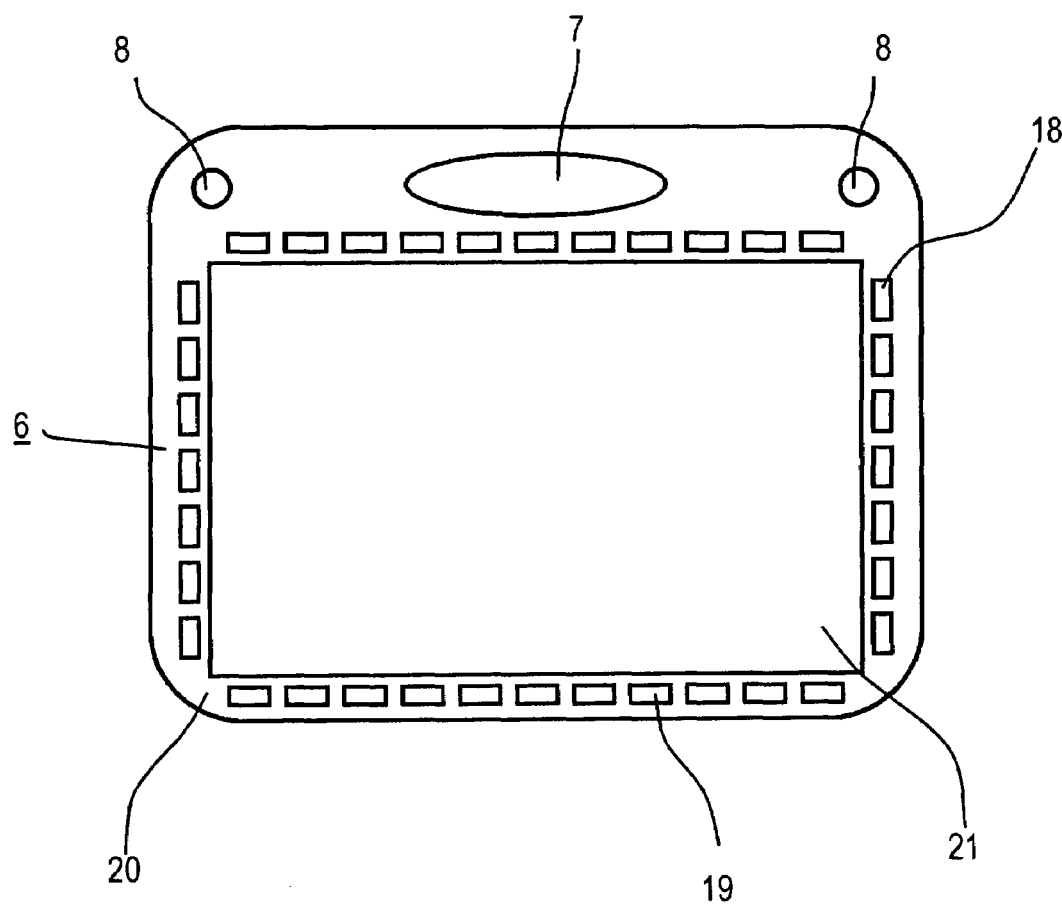
FIG. 3 shows a flat X-ray detector according to at least one embodiment of the invention having two gripping holes.

FIG. 3 illustrates a first embodiment of a mobile flat X-ray detector 6 according to at least one embodiment of the invention. The pixel matrix with an active surface 21 is located in a detector housing 20. The driving circuits 18 and the readout electronics 19 are arranged next to the active surface 21. The spacing between the edge of the active surface 21 and the edge of the detector housing 20 is wider in the upper region such that this region is designed in the form of a grip 7. In addition to the grip 7, finger size gripping elements, for example gripping holes 8, depressions, pits and/or gripping troughs, are arranged at the edge of the detector housing 20.

If, as illustrated in FIG. 1, the flat X-ray detector 6 is now pushed below the patient 5, the grip 7 is certainly covered and can no longer be reached by an operator or can be reached only in a very troublesome or difficult way, but the gripping holes 8 project forward somewhat laterally below the patient 5 and allow the operator to draw the flat X-ray detector 6 forward below the patient 5 with the aid of a finger in the gripping hole 8. However, should the patient 5 also be lying on the gripping holes 8, he does not do so with his full weight, but in the region where his curves are already beginning and so he does not fully load the flat X-ray detector 6 in the region of the gripping holes 8.

Figure 4:
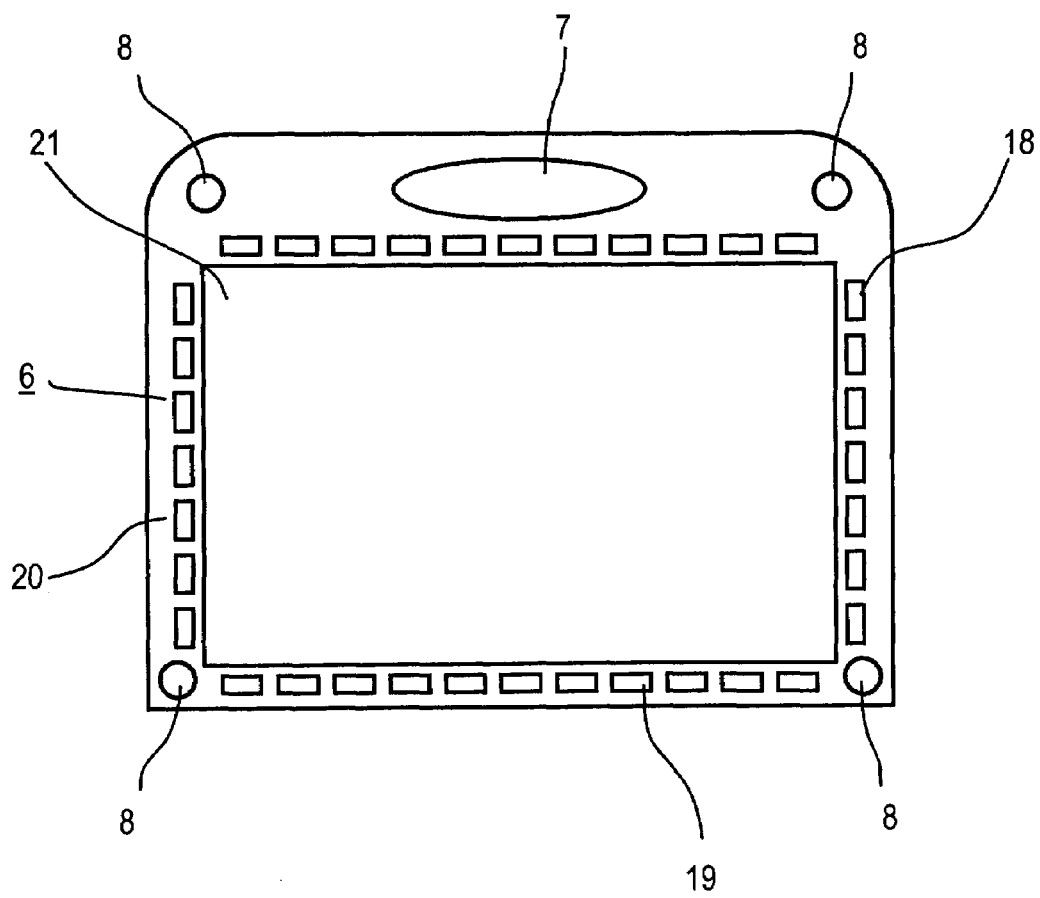
FIG. 4 shows a second embodiment of a flat X-ray detector according to at least one embodiment of the invention having four gripping holes.

Essentially the same flat X-ray detector 6 is illustrated in FIG. 4. As opposed to the previous embodiment, however, the lower corners are not rounded, but are of approximately rectangular design such that here, as well, gripping holes 8 can still be provided.

Figure 5:
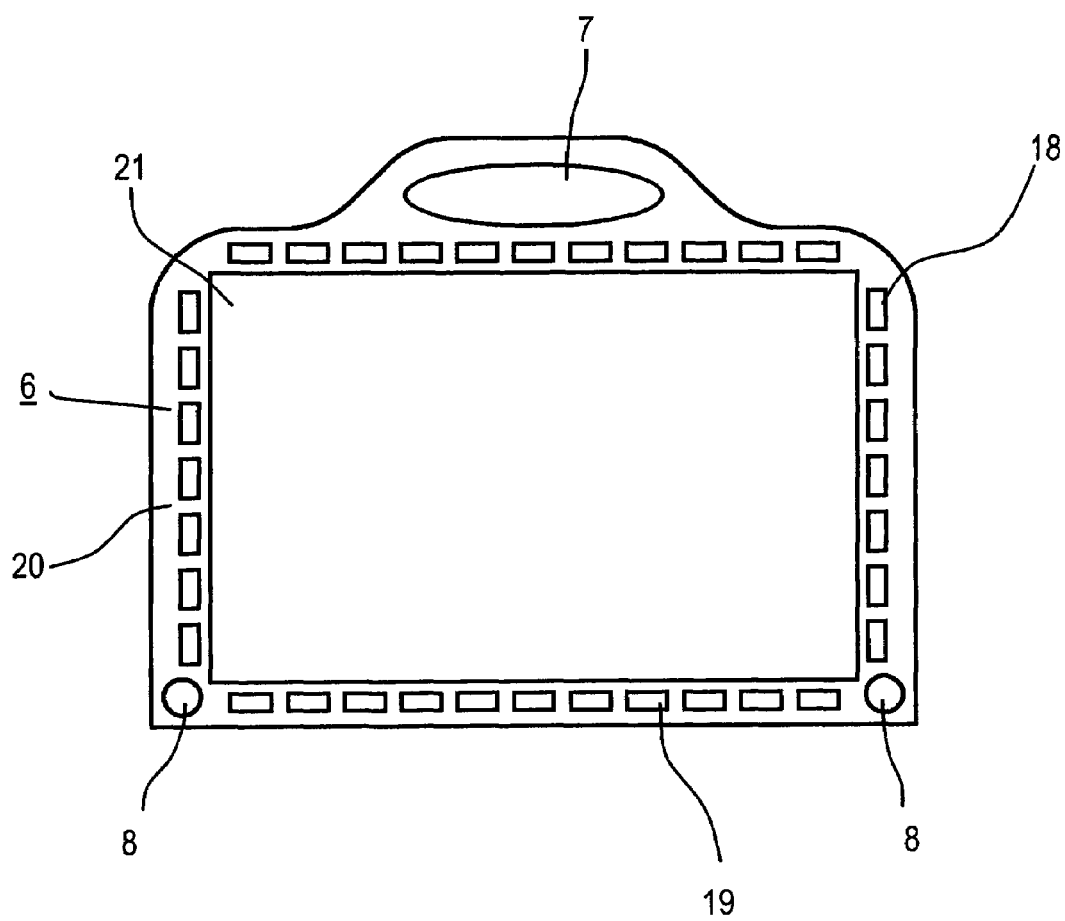
FIG. 5 shows a variant of a flat X-ray detector in accordance with FIG. 3.

FIG. 5 shows a third alternative of the flat X-ray detector 6 according to an embodiment of the invention, in the case of which the grip 7 is designed to project in relation to the detector housing 20. Owing to the curves, no gripping holes 8 can be provided next to the grip 7. They are therefore arranged in the lower region as in the case of the flat X-ray detector 6 in accordance with FIG. 4.

The following advantages accrue owing to the inventive design of the flat X-ray detector 6 in which, apart from the actual grip 7, approximately finger size gripping elements in the form of gripping holes 8, depressions and/or gripping troughs are provided at the edge of the flat X-ray detector 6, outside the active surface 21:

Withdrawal from under the patent becomes very simple.

There is no negative influence on the spacing between the active surface 21 and the outer edge of the flat X-ray detector 6.

The solutions can be employed both for portable flat X-ray detectors with cable, and for flat X-ray detectors 6 without cable.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A transportable flat X-ray detector comprising:
    a housing including an active surface, the active surface including a scintillator layer and semiconductor layer including a multiplicity of pixel elements arranged in a matrix;
    a grip formed entirely within the housing; and
    a plurality of gripping elements provided in the housing at an edge of the flat X-ray detector outside the active surface, wherein the gripping elements are arranged entirely within the corners of the housing of the flat X-ray detector.

2. The transportable flat X-ray detector as claimed in claim 1, wherein the gripping elements include holes.

3. The transportable flat X-ray detector as claimed in claim 2, wherein the gripping elements include at least one of depressions, pits and troughs.

4. The transportable flat X-ray detector as claimed in claim 3, wherein the gripping elements are arranged in the corners of the flat X-ray detector.

5. The transportable flat X-ray detector as claimed in claim 2, wherein the gripping elements are arranged in the corners of the flat X-ray detector.

6. The transportable flat X-ray detector as claimed in claim 2, wherein the gripping elements are arranged on both sides next to the grip.

7. The transportable flat X-ray detector as claimed in claim 2, wherein the gripping elements have a diameter of the size of a finger.

8. The transportable flat X-ray detector as claimed in claim 1, wherein the gripping elements include at least one of depressions, pits and troughs.

9. The transportable flat X-ray detector as claimed in claim 8, wherein the gripping elements are arranged in the corners of the flat X-ray detector.

10. The transportable flat X-ray detector as claimed in claim 8, wherein the gripping elements are arranged on both sides next to the grip.

11. The transportable flat X-ray detector as claimed in claim 8, wherein the gripping elements have a diameter of the size of a figure.

12. The transportable flat X-ray detector as claimed in claim 1, wherein the gripping elements are arranged on both sides next to the grip.

13. The transportable flat X-ray detector as claimed in claim 1, wherein the gripping elements have a diameter of the size of a finger.

14. A transportable flat X-ray detector comprising:
    a housing including,
        a grip,
        an active surface including a multiplicity of pixel elements arranged in a matrix, and
        gripping elements, located at an edge of the flat X-ray detector, outside the active surface, wherein
        the gripping elements are arranged in the corners of the housing of the flat X-ray detector.

15. The transportable flat X-ray detector as claimed in claim 14, wherein the gripping elements include holes.

16. The transportable flat X-ray detector as claimed in claim 14, wherein the gripping elements include at least one of depressions, pits and troughs.

17. The transportable flat X-ray detector as claimed in claim 14, wherein the gripping elements are arranged on both sides next to the grip.

18. The transportable flat X-ray detector as claimed in claim 14, wherein the gripping elements have a diameter of the size of a finger.

19. A transportable flat X-ray detector comprising:

a housing enclosing an active surface, the active surface including a scintillator layer and semiconductor layer including a multiplicity of pixel elements arranged in a matrix;

a plurality of gripping elements formed entirely within the housing outside of the active surface; and at least one handle formed entirely within the housing outside of the active surface, the at least one handle being between at least two gripping elements.

* * * * *